US009643179B1

(12) United States Patent
Engelmann et al.

(10) Patent No.: US 9,643,179 B1
(45) Date of Patent: May 9, 2017

(54) TECHNIQUES FOR FABRICATING HORIZONTALLY ALIGNED NANOCHANNELS FOR MICROFLUIDICS AND BIOSENSORS

(71) Applicant: International Business Machines Corporation, Armonk, NY (US)

(72) Inventors: Sebastian U. Engelmann, White Plains, NY (US); Stephen M. Rossnagel, Pleasantville, NY (US); Ying Zhang, Sunnyvale, CA (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/192,281

(22) Filed: Jun. 24, 2016

(51) Int. Cl.
*G01N 27/403* (2006.01)
*B01L 3/00* (2006.01)
*B82B 1/00* (2006.01)
*B82B 3/00* (2006.01)

(52) U.S. Cl.
CPC ... *B01L 3/502707* (2013.01); *B01L 3/502715* (2013.01); *B82B 1/005* (2013.01); *B82B 3/008* (2013.01); *B01L 2200/12* (2013.01); *B01L 2300/0858* (2013.01); *B01L 2300/0861* (2013.01); *B01L 2300/0887* (2013.01); *B01L 2300/0896* (2013.01); *B01L 2300/12* (2013.01)

(58) Field of Classification Search
CPC ......... B01L 3/502707; B01L 3/502715; B01L 2200/12; B01L 2300/0858; B01L 2300/0861; B01L 2300/12; B82B 1/005
See application file for complete search history.

(56) References Cited

U.S. PATENT DOCUMENTS

| 8,414,785 B2 | 4/2013 | Walker et al. |
| 8,652,337 B1 | 2/2014 | Afzali-Ardakani et al. |
| 8,945,404 B2 | 2/2015 | Afzali-Ardakani et al. |

(Continued)

FOREIGN PATENT DOCUMENTS

| KR | 101120940 B1 | 3/2012 |
| WO | WO2011078650 A2 | 6/2011 |

OTHER PUBLICATIONS

English Abstract Translation of KR101120940B1 by Kim Woong et al. Mar. 5, 2012.

(Continued)

*Primary Examiner* — Yosef Gebreyesus
(74) *Attorney, Agent, or Firm* — Louis J. Percello; Michael J. Chang, LLC

(57) ABSTRACT

Techniques for fabricating horizontally aligned nanochannels are provided. In one aspect, a method of forming a device having nanochannels is provided. The method includes: providing a SOI wafer having a SOI layer on a buried insulator; forming at least one nanowire and pads in the SOI layer, wherein the nanowire is attached at opposite ends thereof to the pads, and wherein the nanowire is suspended over the buried insulator; forming a mask over the pads, the mask having a gap therein where the nanowire is exposed between the pads; forming an alternating series of metal layers and insulator layers alongside one another within the gap and surrounding the nanowire; and removing the nanowire to form at least one of the nanochannels in the alternating series of the metal layers and insulator layers. A device having nanochannels is also provided.

20 Claims, 6 Drawing Sheets

FIG. 35 metal/insulator layers

3402

(56) References Cited

U.S. PATENT DOCUMENTS

| | | |
|---|---|---|
| 9,059,135 B2 | 6/2015 | Bai et al. |
| 2006/0001039 A1 | 1/2006 | Zamanian |
| 2007/0122313 A1 | 5/2007 | Li et al. |
| 2011/0133167 A1* | 6/2011 | Bangsaruntip ......... B82Y 10/00 257/24 |
| 2013/0224915 A1* | 8/2013 | Sleight .............. H01L 29/66477 438/197 |
| 2013/0224924 A1* | 8/2013 | Sleight .............. H01L 29/66477 438/284 |
| 2014/0197370 A1* | 7/2014 | Leobandung ..... H01L 29/66439 257/9 |
| 2014/0370667 A1* | 12/2014 | Sleight .................. H01L 29/775 438/151 |

OTHER PUBLICATIONS

Choi et al., "Fabrication of Buried Nanochannels by Transferring Metal Nanowire Patterns," Sensors and Materials, vol. 21, No. 6, pp. 315-319 (Jan. 2009).

NASA Tech Briefs, "Fabrication of Buried Nanochannels From Nanowire Patterns," Friday, Jun. 29, 2007 (2 pages).

Gong et al., "Fabrication of nanochannels with water-dissolvable nanowires," Nanotechnology. (Apr. 21, 2010) (6 pages).

* cited by examiner

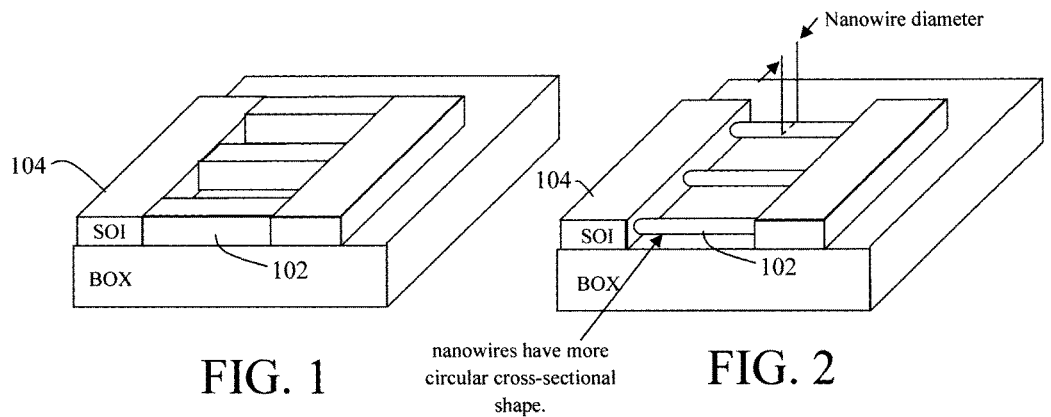
FIG. 1
FIG. 2
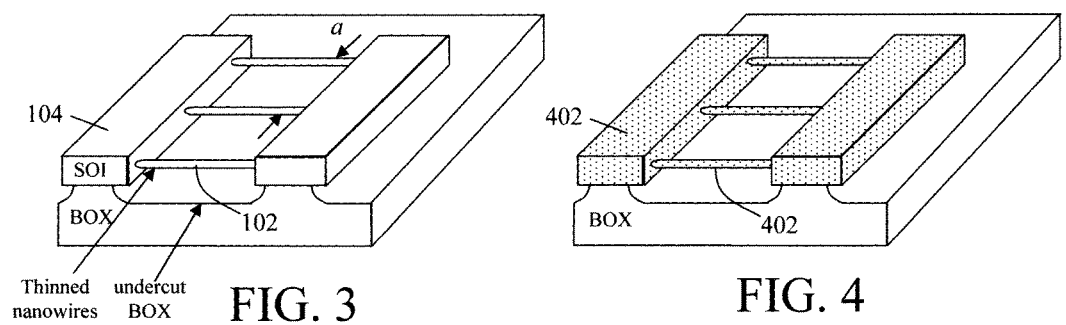
FIG. 3
FIG. 4
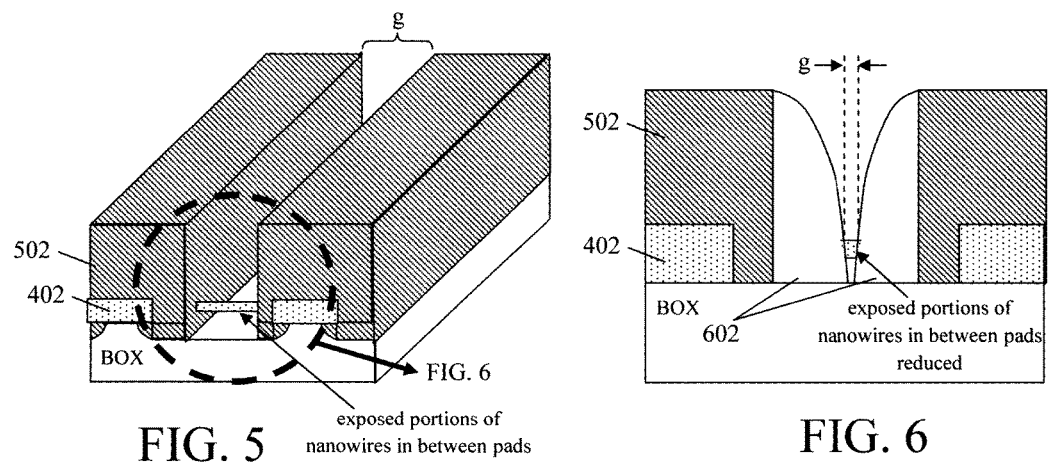
FIG. 5
FIG. 6 insulator removed from horizontal surfaces using anisotropic etch

TECHNIQUES FOR FABRICATING HORIZONTALLY ALIGNED NANOCHANNELS FOR MICROFLUIDICS AND BIOSENSORS

FIELD OF THE INVENTION

The present invention relates to devices having nanochannels, and more particularly, to techniques for fabricating horizontally aligned nanochannels.

BACKGROUND OF THE INVENTION

Nanochannels or nanopores with ultra-thin alternating layer properties (i.e., multi-layers of insulator/metal) are very challenging to be fabricated in the nanoscale range (e.g., less than 10 nanometer (nm) channel diameter). While solutions exist to fabricate vertically aligned nanochannels/nanopores, for instance, using highly focused electron beam (e-beam), such as the e-beams used in ultra-high resolution transmission electron microscopy (TEM) systems, to drill individual nanopores on a very small sample, typical sample sizes being less than 10 millimeters (mm)×10 mm, these devices are not ideal from an application point of view.

Furthermore, the solutions are not compatible with large scale integration, thus preventing the advantage of lowering production costs. For example, biosensors that are able to electrically scan genomes are fabricated by atomic layer deposition (ALD) of metal/insulators, in which holes are drilled to form the nanofluidic channel. The hole drilling process is not compatible with large scale integration, and also the vertical alignment is unfavorable. This makes the fabrication of these biosensors very expensive and is in contrast to the original idea that processing sensors using silicon process technology would bring down the cost per sensor.

Accordingly, improved techniques for fabricating horizontally aligned nanochannels would be desirable.

SUMMARY OF THE INVENTION

The present invention provides techniques for fabricating horizontally aligned nanochannels. In one aspect of the invention, a method of forming a device having nanochannels is provided. The method includes: providing a silicon-on-insulator (SOI) wafer having a SOI layer on a buried insulator; forming at least one nanowire and pads in the SOI layer, wherein the nanowire is attached at opposite ends thereof to the pads, and wherein the nanowire is suspended over the buried insulator; forming a mask over the pads, the mask having a gap therein where the nanowire is exposed between the pads; forming an alternating series of metal layers and insulator layers alongside one another within the gap and surrounding the nanowire; and removing the nanowire to form at least one of the nanochannels in the alternating series of the metal layers and insulator layers.

In another aspect of the invention, a device is provided. The device includes: an alternating series of metal layers and insulator layers alongside one another on a buried insulator; and a plurality of nanochannels that are horizontally aligned through the series of metal layers and insulator layers.

A more complete understanding of the present invention, as well as further features and advantages of the present invention, will be obtained by reference to the following detailed description and drawings.

BRIEF DESCRIPTION OF THE DRAWINGS

FIG. 1 is a three-dimensional diagram illustrating a plurality of nanowires and pads having been patterned in a silicon-on-insulator (SOI) wafer according to an embodiment of the present invention;

FIG. 2 is a three-dimensional diagram illustrating the nanowires having been reshaped according to an embodiment of the present invention;

FIG. 3 is a three-dimensional diagram illustrating a recess etch of the buried insulator having been performed and the nanowires having been thinned according to an embodiment of the present invention;

FIG. 4 is a three-dimensional diagram illustrating a (conformal) dielectric having been deposited onto the nanowires and pads according to an embodiment of the present invention;

FIG. 5 is a three-dimensional diagram illustrating a patterned mask having been formed over the pads with a gap therein where the nanowires are exposed between the pads according to an embodiment of the present invention;

FIG. 6 is a cross-sectional diagram illustrating spacers having been formed in the gap, narrowing the gap, according to an embodiment of the present invention;

DETAILED DESCRIPTION OF PREFERRED EMBODIMENTS

Figure 7:
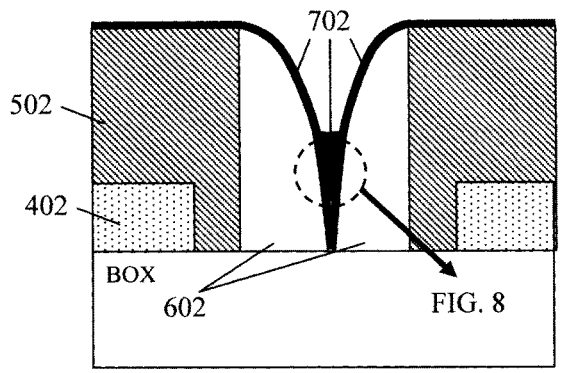
FIG. 7 is a cross-sectional diagram illustrating a metal having been deposited into the remaining gap, covering a central portion of the nanowires according to an embodiment of the present invention.

Provided herein are techniques for fabricating horizontally aligned nanochannels useful for a variety of applications. As will be described in detail below, the present techniques leverage the accessibility of a nanowire to recess a whole layer of thickness d from the nanowire, where etching on the extent of d/2 occurs from 2 fronts. The same amount of etch has to be expected on the sidewall, leaving d/2 of the original deposited thickness d on the sidewall. By repeating the above procedure, alternating layers of very fine thickness can be deposited around a dummy wire. The dummy wire can then be selectively removed to form the nanofluidic nanochannels.

A first exemplary embodiment of the present techniques are now described in detail by way of reference to FIGS. 1-26. As shown in FIG. 1, the process begins with a wafer in which at least one nanowire 102 has been defined. According to the exemplary embodiment shown illustrated in the figures, the starting wafer is a silicon-on-insulator (SOI) wafer. As is known in the art, a SOI wafer includes an SOI layer on a buried insulator. When the buried insulator is an oxide (as in the present example), it is often referred to as a buried oxide or BOX. The buried insulator often separates the SOI layer from a substrate (not shown).

A plurality of the nanowires 102 are then patterned in the SOI layer. As highlighted above, these nanowires 102 will, when selectively removed, form a plurality of nanochannels. In the example shown, the plurality of nanowires 102 are attached, at opposite ends thereof, to pads 104. Namely, the SOI layer has been patterned with the nanowires 102 and pads 104 having a ladder-like configuration with the nanowires 102 appearing as the rungs of a ladder. Standard lithography and etching techniques may be employed.

Next, as shown in FIG. 2, it may be preferable to reshape the nanowires 102. Namely, reshaping the nanowires 102 can give them a circular cross-sectional shape (see FIG. 2), as compared to their square as-patterned shape (see FIG. 1). According to an exemplary embodiment, the nanowires 102 are reshaped using a hydrogen ($H_2$) annealing process which smoothes the nanowire sidewalls and reshapes the nanowire cross-section from a rectangular cross-section to a more circular cross-section. As described below, an $H_2$ anneal can also be used to thin the nanowire bodies by re-distributing silicon from the nanowires 102 to the pads 104. According to an exemplary embodiment, the $H_2$ annealing is performed with a gas pressure of from about 30 torr to about 1,000 torr, at a temperature of from about 600 degrees Celsius (° C.) to about 1,100° C., and ranges therebetween, for a duration of from about one minute to about 120 minutes, and ranges therebetween. In general, the rate of Si re-distribution increases with temperature and decreases with an increase in pressure. For a discussion of the nanowire reshaping and thinning process see, for example, U.S. Pat. No. 7,884,004 issued to Bangsaruntip et al., entitled "Maskless Process for Suspending and Thinning Nanowires," the contents of which are incorporated by reference as if fully set forth herein.

By way of example only, the nanowires described herein are structures having an aspect ratio (length-to-diameter) of from about 5 to about 12, and ranges therebetween. Following reshaping, nanowires 102 can have a diameter of from about 20 nanometers (nm) to about 30 nm, and ranges therebetween. As will be described in detail below, if so desired, the nanowires 102 can also be thinned. Thinning the nanowires 102 reduces the size of the nanochannels formed when the nanowires 102 are removed (see below). According to an exemplary embodiment, once thinned, the diameter of the nanowires 102 is reduced to from about 10 nm to about 20 nm, and ranges therebetween.

In order to fully access the circumference of the nanowires 102, a recess etch of the buried insulator (the BOX in this example) is next performed. See FIG. 3. An anisotropic etch (such as an oxide-selective reactive ion etch or RIE) can be used to undercut the BOX beneath the nanowires 102. Following the undercut etch, the nanowires 102 can be thinned, if so desired. As mentioned, the above-described $H_2$ annealing process can also be employed to thin the nanowire bodies by re-distributing silicon from the nanowires 102 to the pads 104. The conditions for this anneal were provided above.

The result is a plurality of horizontally aligned nanowires 102. Namely, as shown in FIG. 3, the nanowires 102 can be spaced apart from each other horizontally by a regular distance a, wherein a is from about 1 nm to about 5 nm, and ranges therebetween. These nanowires arranged in this manner will serve as the basis for forming a plurality of horizontally aligned nanochannels (see below).

It is notable that a release of the nanowires from the underlying buried oxide can also be achieved by the thinning of the nanowires 102. Namely, as-patterned, the nanowires 102 are resting on the buried insulator. However, as the nanowires 102 are thinned, the material removed from the circumference of the nanowires 102 causes the nanowires 102 to pull away from the underlying buried insulator. Thus, if thinned enough, the result can be a suspended nanowire. Accordingly, it is possible to perform the reshaping (FIG. 2), thinning and suspending (FIG. 3) altogether via one $H_2$ anneal step, wherein redistribution of the nanowire material results in more circular, thinner nanowires that have pulled away from the buried insulator.

A dielectric 402 is then deposited onto the nanowires 102 and pads 104. See FIG. 4. Suitable dielectrics include, but are not limited to, high-κ dielectrics such as lanthanum oxide ($LaO_2$) and hafnium oxide ($HfO_2$). The term "high-κ" as used herein refers to a material having a relative dielectric constant κ which is much higher than that of silicon dioxide (e.g., a dielectric constant κ=25 for $HfO_2$ rather than 4 for silicon dioxide). As shown in FIG. 4, the dielectric 402 can be deposited as a conformal layer on the nanowires 102 and pads 104. Suitable conformal deposition processes include, but are not limited to, atomic layer deposition (ALD). Dielectric 402 serves as additional etch stop for the metal/insulator etches (see below). While dielectric 402 is preferred for this purpose, its presence is not essential.

A patterned mask 502 is then formed over the pads 104 with a gap g therein where the nanowires 102 are exposed. See FIG. 5. The notion here is to leave only portions of the nanowires 102 between the pads 104 exposed/not covered by the mask 502. Suitable hardmask materials for forming mask 502 include, but are not limited to, nitride materials, such as silicon nitride (SiN). Standard lithography and etching techniques can be used to pattern the mask 502.

Spacers 602 are then formed in the gap. See FIG. 6. FIG. 6 is a cross-sectional view along the nanowire array. Placing the spacers 602 in the gap permits the gap g between the pads to be narrowed such that only a small central portion of nanowires remains exposed. By way of example only, following formation of the spacers, the gap g is from about 2 nanometers (nm) to about 10 nm, and ranges therebetween.

Spacers 602 can be formed by depositing a spacer material into the gap, and then patterning the spacer material into the individual spacers 602. Suitable spacer materials include, but are not limited to, a nitride material (such as SiN) and/or an oxide material (such as silicon oxide ($SiO_2$)).

A metal 702 is then deposited into the remaining gap g (between the spacers 602) and covering the central portions of the nanowires 102. See FIG. 7. The goal here will be to create nanochannels in ultra-thin layers with alternating properties, e.g., multiple, alternating layers of insulator and metal. Metal 702 will be used to form one of the ultra-thin metal layers. Suitable metals for metal 702 include, but are not limited to, titanium nitride (TiN), tantalum nitride (TaN), tungsten (W), etc. A conformal deposition process, such as ALD, can be used to deposit the metal 702 into the gap.

Figure 8:
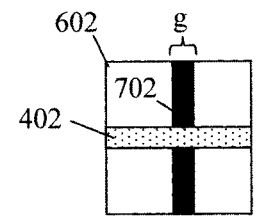
FIG. 8 is a cross-sectional view through the nanowires in the structure of FIG. 7 according to an embodiment of the present invention.
Figure 9:
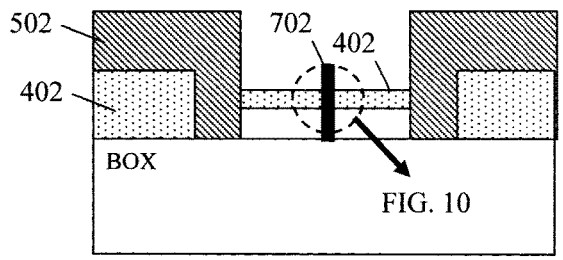
FIG. 9 is a cross-sectional diagram illustrating the spacers having been removed according to an embodiment of the present invention.

A cross-sectional view through the nanowires is shown in FIG. 8. As shown in FIG. 8, the metal 702 is present in the gap g between the spacers 602, both above and below the nanowires 102 (which are covered in dielectric 402).

After the deposition of metal 702, the spacers 602 can be removed. See FIG. 9. Spacers 602 can be removed using a selective etch. For instance, if the spacers 602 are oxide spacers and the mask 502 is a nitride hardmask, then an oxide-selective reactive ion etch or RIE can be used to fully remove the spacers 602 selective to the mask 502. However, depending on the level of selectivity of the etch, a portion of the mask 502 may end up being removed during the spacer etch (although to a lesser degree than the spacers). See FIG. 9.

Use of the spacers 602 permitted placement of the layer of metal 702 over the central portions of the nanowires 102. After that, removing the spacers 602 opens the gap g in the mask 502 between the pads 104, which will permit alternating layers of insulator and metal to be placed alongside one another within the gap, both at the sidewalls of the mask and at the sidewalls of the metal layer 702. See below.

Figure 10:
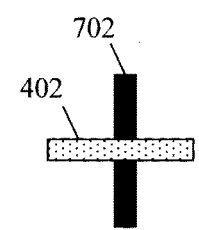
FIG. 10 is a cross-sectional view through the nanowires in the structure of FIG. 9 according to an embodiment of the present invention.

A cross-sectional view through the nanowires is shown in FIG. 10. As shown in FIG. 10, an ultra-thin layer of the metal 702 is now present surrounding the nanowires 102 (which are covered in dielectric 402). According to an exemplary embodiment, this ultra-thin layer of the metal 702 has a thickness of from about 2 nm to about 10 nm, and ranges therebetween.

Figure 11:
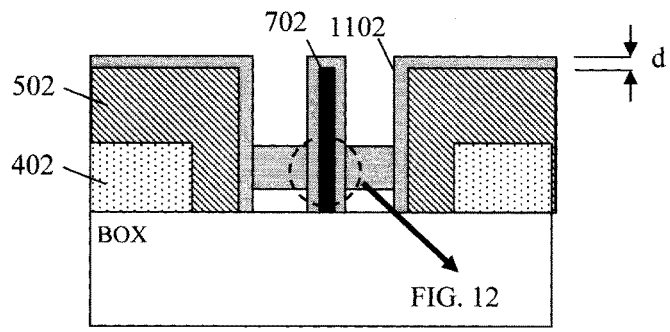
FIG. 11 is a cross-sectional diagram illustrating an insulator having been deposited on the top and sidewalls of the mask, on the top and sidewalls of the metal layer, and surrounding the exposed portions of the nanowires according to an embodiment of the present invention.

The next layer deposited is an insulator. See FIG. 11. Specifically, as shown in FIG. 11 a layer of an insulator 1102 is deposited on the top and sidewalls of the mask 502, on the top and sidewalls of the layer of metal 702, and surrounding the exposed portions of the nanowires 102. Suitable insulators include, but are not limited to, oxides (such as silicon oxide (SiOx), hafnium oxide ($HfO_2$), silicon nitride (SiN), aluminum oxide ($Al_2O_3$), etc.). A conformal deposition process, such as ALD, can be used to deposit the insulator 1102. According to an exemplary embodiment, insulator 1102 is deposited to a thickness d of from about 2 nm to about 10 nm, and ranges therebetween.

Figure 12:
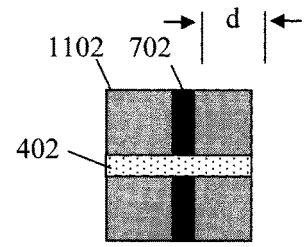
FIG. 12 is a cross-sectional view through the nanowires in the structure of FIG. 11 according to an embodiment of the present invention.

A cross-sectional view through the nanowires is shown in FIG. 12. As shown in FIG. 12, alternating layers of metal 702 and insulator 1102 are now present surrounding the nanowires 102 (which are covered in dielectric 402).

Figure 13:
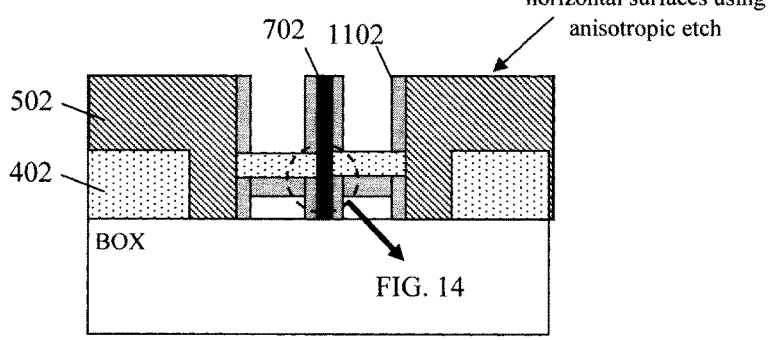
FIG. 13 is a cross-sectional diagram illustrating an anisotropic etch having been used to remove the deposited insulator from all horizontal surfaces according to an embodiment of the present invention.

A directional (anisotropic) etch followed by an non-directional (isotropic) etch is then used to remove the insulator from horizontal surfaces and thin the insulator, respectively. Namely, as shown in FIG. 13, an anisotropic etch is used to remove the deposited insulator 1102 from all horizontal surfaces (i.e., following this etch, the insulator 1102 is only present on vertical surfaces), including the horizontal surfaces of the nanowires 102. RIE, for example, is a suitable anisotropic etching process. By way of example only, if the insulator is an oxide material, then an oxide-selective RIE can be employed in this step.

Figure 14:
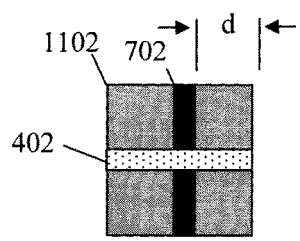
FIG. 14 is a cross-sectional view through the nanowires in the structure of FIG. 13 according to an embodiment of the present invention.
Figure 15:
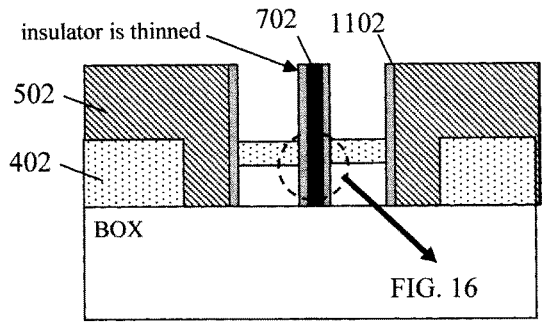
FIG. 15 is a cross-sectional diagram illustrating an isotropic etch having been used to thin the insulator according to an embodiment of the present invention.

A cross-sectional view through the nanowires is shown in FIG. 14. As shown in FIG. 14, the insulator 1102 that remains on the vertical surfaces has a thickness d.

Next, an isotropic etch is used to thin the insulator 1102 that remains on the vertical surfaces. See FIG. 15. A suitable isotropic etching process includes, but is not limited to, a wet etching process. By way of example only, if the insulator is an oxide material, then a buffered oxide etch or BOE can be employed in this step. This thinning etch can be easily regulated. For instance, one can regulate the thickness of the material via the thinning etch to be d/2 by knowing the etch rate and using that to calibrating the etching process.

Figure 16:
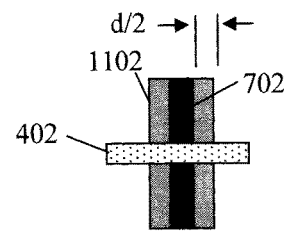
FIG. 16 is a cross-sectional view through the nanowires in the structure of FIG. 15 according to an embodiment of the present invention.

A cross-sectional view through the nanowires is shown in FIG. 16. As shown in FIG. 16, with an isotropic etch insulator removal is expected on all sidewalls, leaving d/2 of the original deposited thickness on the sidewalls. Thus, the goal is to reduce the thickness of the insulator by about half Thus, to use a simple example, if d is 5 nm, then following the thinning etch d/2=2.5 nm.

Figure 17:
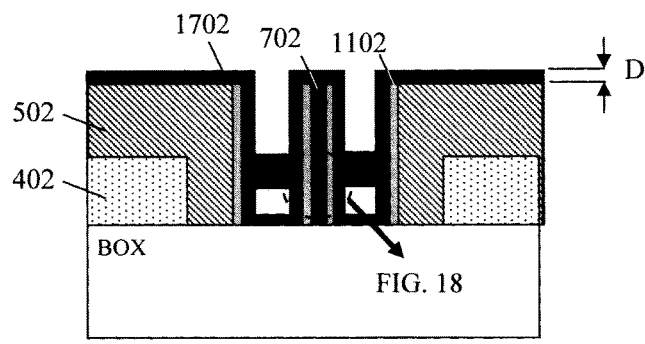
FIG. 17 is a cross-sectional diagram illustrating another layer of metal having been deposited on the top and sidewalls of the mask, on the top and sidewalls of the existing metal/insulator series, and surrounding the exposed portions of the nanowires according to an embodiment of the present invention.

As provided above, the goal is to produce a series of layers with alternating properties, e.g., multiple, alternating layers of insulator and metal. Thus, the next layer deposited is another metal layer 1702. See FIG. 17. Specifically, as shown in FIG. 17 a layer of the metal 1702 is deposited on the top and sidewalls of the mask 502, on the top and sidewalls of the metal 702/insulator 1102 series, and surrounding the exposed portions of the nanowires 102. Suitable metals were provided above. According to an exemplary embodiment, the same metal or insulator is placed at each iteration. However, this is not a requirement, and the metal and/or insulator composition can be varied throughout the series, if so desired. A conformal deposition process, such as ALD, can be used to deposit the metal layer 1702. According to an exemplary embodiment, metal 1702 is deposited to a thickness D of from about 2 nm to about 10 nm, and ranges therebetween.

Figure 18:
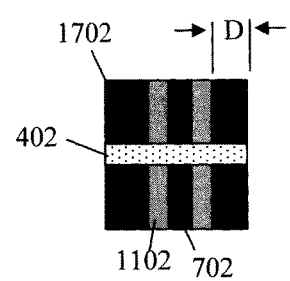
FIG. 18 is a cross-sectional view through the nanowires in the structure of FIG. 17 according to an embodiment of the present invention.
Figure 19:
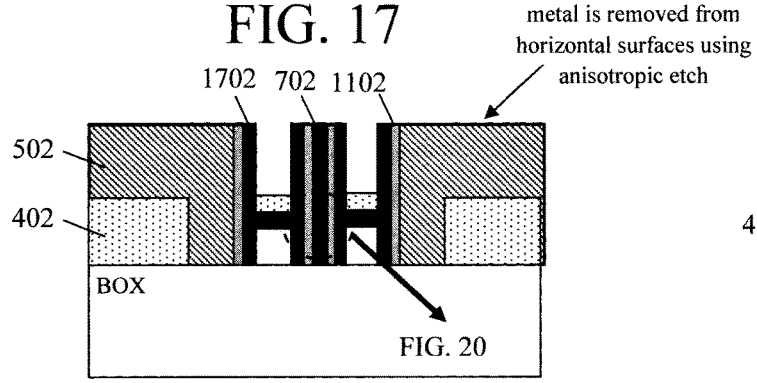
FIG. 19 is a cross-sectional diagram illustrating an anisotropic etch having been used to remove the deposited metal from all horizontal surfaces according to an embodiment of the present invention.

A cross-sectional view through the nanowires is shown in FIG. 18. As shown in FIG. 18, alternating layers of metal 702/1702 and insulator 1102 are now present surrounding the nanowires 102 (which are covered in dielectric 402).

In the same manner as described above, an anisotropic etch (e.g., RIE) is used to remove the deposited metal 1702 from all horizontal surfaces (including the horizontal surfaces of the nanowires 102) such that, following the etch, the insulator 1702 is present only on vertical surfaces. See FIG. 19.

Figure 20:
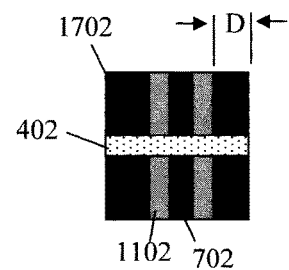
FIG. 20 is a cross-sectional view through the nanowires in the structure of FIG. 19 according to an embodiment of the present invention.
Figure 21:
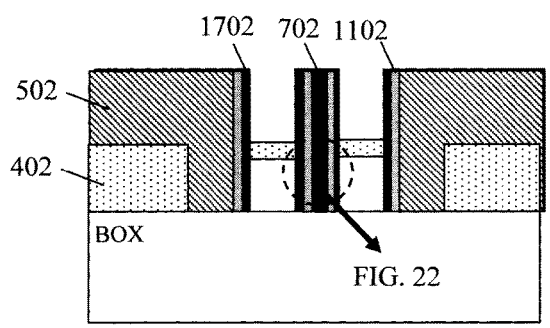
FIG. 21 is a cross-sectional diagram illustrating an isotropic etch having been used to thin the metal according to an embodiment of the present invention.

A cross-sectional view through the nanowires is shown in FIG. 20. As shown in FIG. 20, the metal 1702 that remains on the vertical surfaces has a thickness D.

Figure 22:
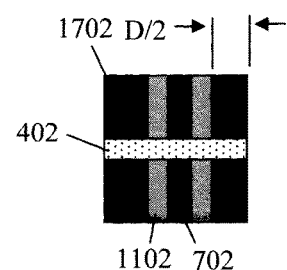
FIG. 22 is a cross-sectional view through the nanowires in the structure of FIG. 21 according to an embodiment of the present invention.
Figure 23:
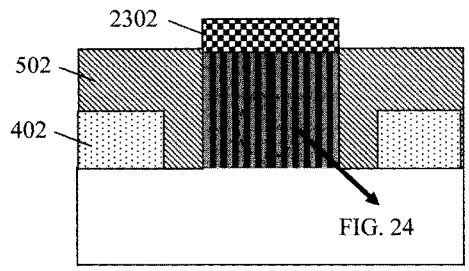
FIG. 23 is a cross-sectional diagram illustrating additional metal/insulator layers having been added, and a hardmask having been formed on the series of metal/insulator layers according to an embodiment of the present invention.

Next, an isotropic etch (e.g., a wet etch) is used to thin the metal 1702 that remains on the vertical surfaces. See FIG. 21. A cross-sectional view through the nanowires is shown in FIG. 22. As shown in FIG. 22 with an isotropic etch, metal removal is expected on all sidewalls, leaving D/2 of the original deposited thickness on the sidewalls.

The process shown in FIGS. 11-22 and described above can be repeated n times to increase the number of alternating insulator and metal layers in the series surrounding the nanowires 102. At each iteration, another insulator or metal layer will be added to the series. According to an exemplary embodiment, the metal/insulator layers are added until the gap in the mask 502 is completely filled. See FIG. 23.

Figure 24:
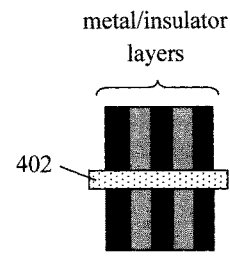
FIG. 24 is a cross-sectional view through the nanowires in the structure of FIG. 23 according to an embodiment of the present invention.
Figure 25:
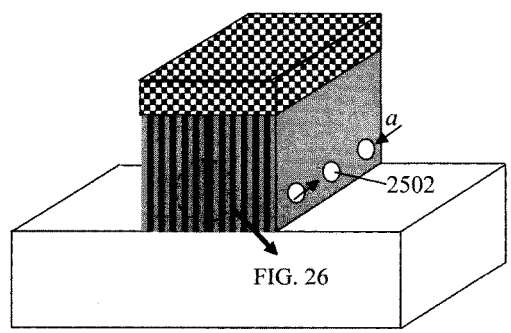
FIG. 25 is a three-dimensional diagram illustrating the mask having been removed, and the nanowires having been selectively removed leaving behind horizontally aligned nanochannels in the metal/insulator layers where the nanowires had been according to an embodiment of the present invention.

At this point in the process, the mask 502 can be removed. Prior to removing mask 502, an additional hardmask 2302 can be formed on the series of metal/insulator layers to protect the metal/insulator layers. See FIG. 23. By way of example only, mask 502 might be silicon (Si), SiN or a similar material, and hardmask 2302 might be a temperature resistant organic planarizing layer (OPL), photoresist, or similar material. These exemplary materials would permit one mask to be removed selective to the other. A cross-sectional view through the nanowires is shown in FIG. 24. As shown in FIG. 24 the nanowires 102 (which are covered in dielectric 402) are embedded in the metal/insulator layers.

Following removal of the mask 502, an isotropic etching process can then be used to remove the nanowires 102 selective to the metal/insulator layers, leaving behind horizontally aligned nanochannels 2502 where the nanowires 102 had been. See FIG. 25. Dielectric 402, if present, also gets removed at this stage. Namely, due to the horizontal alignment of the patterned nanowires 102, the resulting nanochannels 2502 will too be horizontally aligned through the metal/insulator layers. By way of example only, based on a regular spacing of the nanowires 102 (see above), the nanochannels 2502 can also be spaced apart from each other horizontally by a regular distance a, wherein a is from about 1 nm to about 5 nm, and ranges therebetween. Further, as provided above, the nanowires 102 can be configured to have circular cross-sectional shape. Since the nanochannels 2502 are impressions of the nanowires 102 through the metal/insulator layers, the nanochannels 2502 too have a circular cross-sectional shape.

Figure 26:
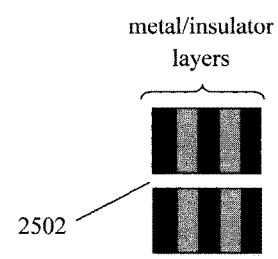
FIG. 26 is a cross-sectional view through the nanowires in the structure of FIG. 25 according to an embodiment of the present invention.
Figure 27:
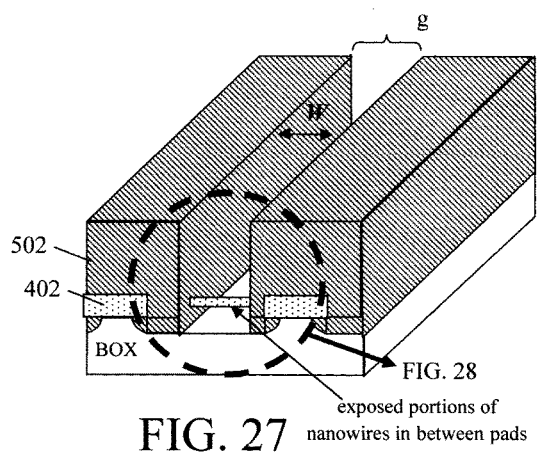
FIG. 27 is a three-dimensional diagram illustrating a starting structure for an alternative embodiment wherein nanowires and pads have been patterned in an SOI layer of an SOI wafer, the nanowires have been reshaped, thinned, and suspended over the underlying buried insulator, and a mask has been formed over the pads with a gap therein where the nanowires are exposed between the pads according to an embodiment of the present invention.

A cross-sectional view through the nanowires is shown in FIG. 26. As shown in FIG. 26, the nanochannels 2502 are present through the metal/insulator layers.

In the exemplary embodiment just presented, placement of the metal and insulator layers begins over a central portion of the nanowires and the series is built layer-by-layer into and out from the center. This, however, requires the use of spacers, an anisotropic etch after the deposition of each layer, etc. An alternative method is now presented by way of reference to FIGS. 27-35 wherein a width of the gap in the mask 502 is set to the final desired device width, and the metal and insulator layers are conformally deposited next to one another in the gap.

The process begins in the same general manner as described above, wherein nanowires 102 (and pads) are patterned in an SOI layer of an SOI wafer, the nanowires 102 are reshaped, thinned, suspended over the underlying buried insulator, and the nanowires 102 and pads are covered in a dielectric 402 (e.g., a high-κ dielectric). A mask 502 is then formed over the pads with a gap therein where the nanowires are exposed between the pads. This is the structure shown in FIG. 27. It is notable that a width W of the gap g should be set to the width for the final device. The reason for this is that in this exemplary embodiment, the resulting final device should be metal/insulator/metal/insulator, etc. rather than, e.g., metal/insulator/metal/metal/insulator/metal. Thus, based on the desired thickness of these metal and insulator layers, one can configure the gap to accommodate the correct sequence of these metal and insulator layers.

Figure 28:
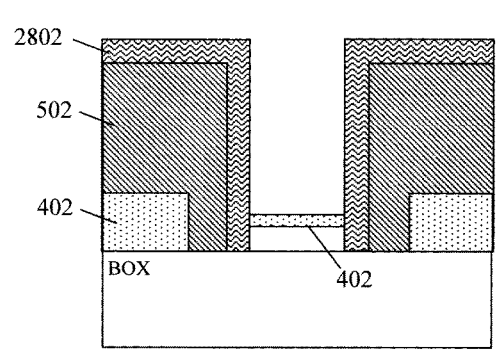
FIG. 28 is a cross-sectional view through the nanowires in the structure of FIG. 27 which illustrates a layer of an insulator having been deposited on the top and sidewalls of the mask, surrounding the nanowires according to an embodiment of the present invention.
Figure 29:
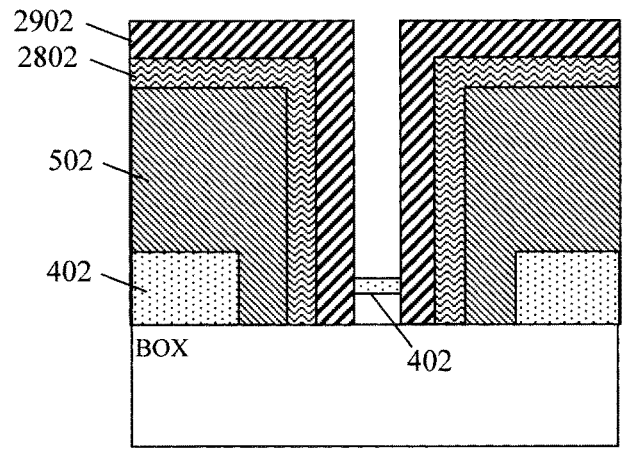
FIG. 29 is a cross-sectional diagram illustrating a layer of a metal having deposited on the insulator according to an embodiment of the present invention.
Figure 30:
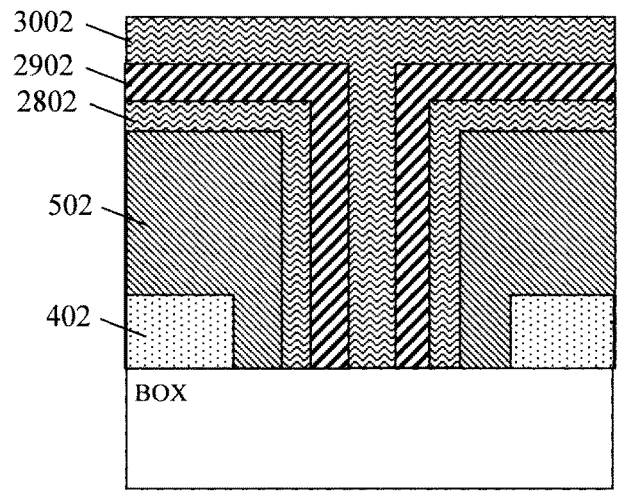
FIG. 30 is a cross-sectional diagram illustrating another insulator layer having been deposited, filling the gap according to an embodiment of the present invention.
Figure 31:
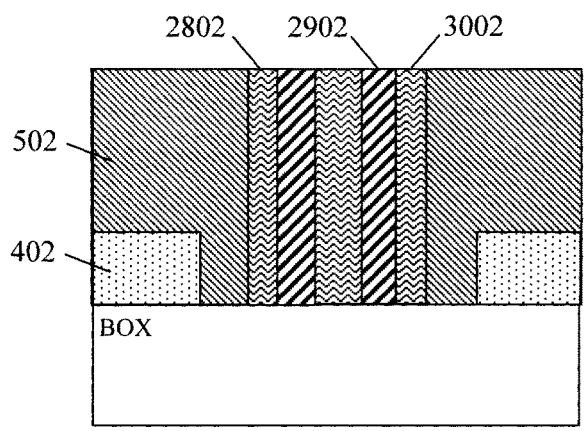
FIG. 31 is a cross-sectional diagram illustrating an etchback of the metal and insulator layers having been performed to remove these materials from the top of the mask according to an embodiment of the present invention.
Figure 32:
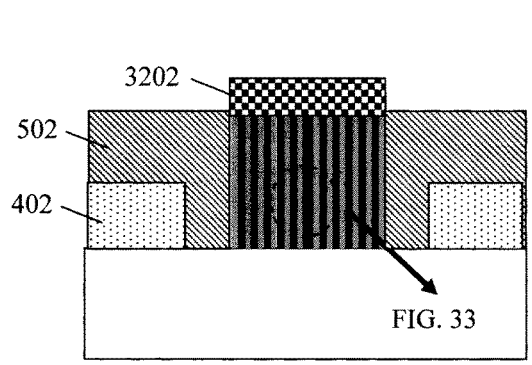
FIG. 32 is a cross-sectional diagram illustrating a hardmask having been formed on the series of metal/insulator layers according to an embodiment of the present invention.

At this point, the processes differ. As shown in FIG. 28 (which is a cross-sectional view through the nanowires shown in FIG. 27), a layer of an insulator 2802 is deposited on the top and sidewalls of the mask 502, surrounding the nanowires 102. As provided above, suitable insulators include, but are not limited to, SiOx, SiN, $Al_2O_3$ etc. A conformal deposition process, such as ALD, can be used to deposit the insulator 2802.

Next, a layer of a metal 2902 is deposited on the insulator 2802, surrounding the nanowires 102. See FIG. 29. As provided above, suitable metals include, but are not limited to, TiN, TaN, W, etc. A conformal deposition process, such as ALD, can be used to deposit the metal 2902. This process is repeated wherein an insulator layer or a metal layer is deposited at each iteration, until a series of metal/insulator layers is formed in, and filling the gap g in the mask 502. In the example depicted in the figures, the addition of another insulator layer 3002 fills the gap. See FIG. 30. However, as provided above, the initial width of the gap can be adjusted to control the final dimensions of this series of metal/insulator layers.

An etchback of the metal and insulator layers is then performed to remove these materials from the top of the mask 502. See FIG. 31. According to an exemplary embodiment, a process such as chemical mechanical polishing (CMP) is used. The mask 502 can serve as an etch stop.

Figure 33:
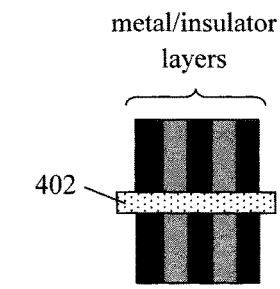
FIG. 33 is a cross-sectional view through the nanowires in the structure of FIG. 32 according to an embodiment of the present invention.
Figure 34:
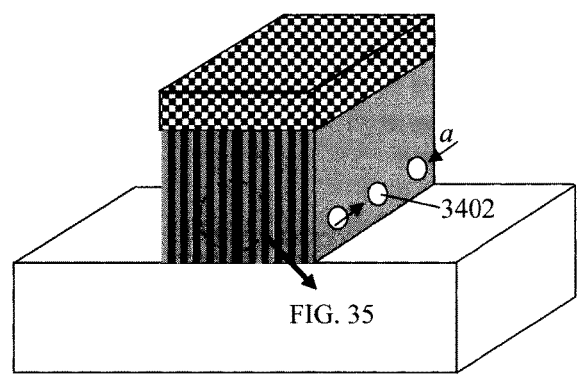
FIG. 34 is a three-dimensional diagram illustrating the mask having been removed, and the nanowires having been selectively removed leaving behind horizontally aligned nanochannels in the metal/insulator layers where the nanowires had been according to an embodiment of the present invention.

The remainder of the process mirrors the exemplary embodiment above. Namely, the mask 502 is removed. Prior to removing mask 502, an additional hardmask 3202 can be formed on the series of metal/insulator layers to protect the metal/insulator layers. See FIG. 32. A cross-sectional view through the nanowires is shown in FIG. 33. As shown in FIG. 33 the nanowires 102 (which are covered in dielectric 402) are embedded in the metal/insulator layers.

Following removal of the mask 502, an isotropic etching process can then be used to remove the nanowires 102 selective to the metal/insulator layers, leaving behind horizontally aligned nanochannels 3402 where the nanowires 102 had been. See FIG. 34. Namely, due to the horizontal alignment of the patterned nanowires 102, the resulting nanochannels 3402 will too be horizontally aligned through the metal/insulator layers. By way of example only, based on a regular spacing of the nanowires 102 (see above), the nanochannels 3402 can also be spaced apart from each other horizontally by a regular distance a, wherein a is from about 1 nm to about 5 nm, and ranges therebetween. Further, as provided above, the nanowires 102 can be configured to have circular cross-sectional shape. Since the nanochannels 3402 are impressions of the nanowires 102 through the metal/insulator layers, the nanochannels 3402 too have a circular cross-sectional shape.

Figure 35:
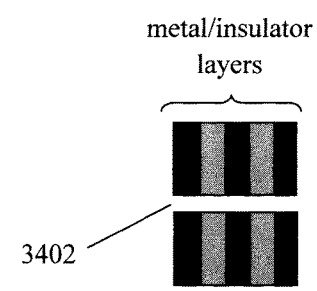
FIG. 35 is a cross-sectional view through the nanowires in the structure of FIG. 34 according to an embodiment of the present invention.

A cross-sectional view through the nanowires is shown in FIG. 35. As shown in FIG. 35, the nanochannels 3402 are present through the metal/insulator layers.

Figure 36:
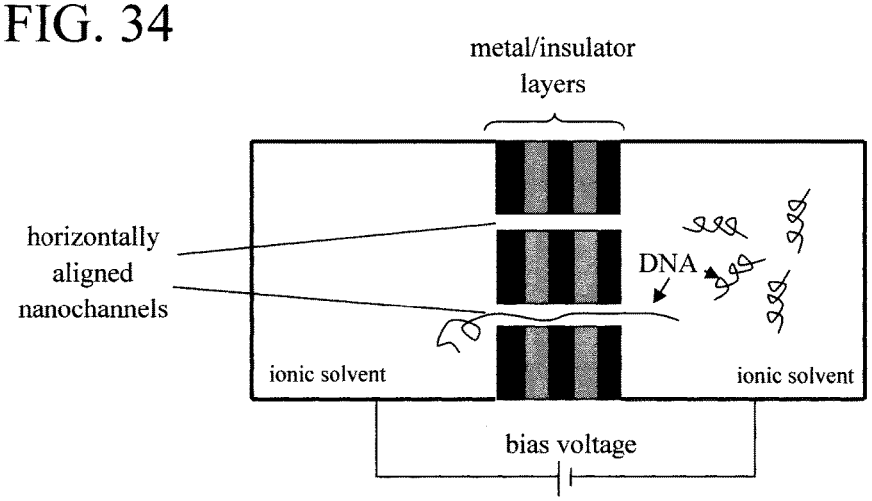
FIG. 36 is a diagram illustrating a biosensor having horizontally aligned nanochannels according to an embodiment of the present invention.

The present techniques can be used to fabricate devices for a variety of applications. By way of example only, the present devices having horizontally aligned nanochannels can be used as biosensors. See, for example, FIG. 36. Biosensors such as deoxy-ribonucleic acid (DNA) transistors are described, for example, in IBM's Icons of Progress, "The DNA Transistor," the contents of which are incorporated by reference as if fully set forth herein. In general, the DNA transistor functions by using an electrical charge to draw strands of genetic material (e.g., DNA) from one reservoir to another through the nanochannels. For instance, a DNA sample (in an ionic solvent) is placed in a reservoir on one side of the nanochannels. A bias voltage (negative on the side with the sample, and positive on the other side) draws strands of the DNA through the nanochannels. As the strands pass through the nanochannels, the combination of the electrical charges and the metal/insulator composition of the membrane have the effect of ratcheting the strands through the channels one bead of genetic material at a time. This mechanism makes it possible to accurately and quickly read the genetic makeup of the strands.

Although illustrative embodiments of the present invention have been described herein, it is to be understood that the invention is not limited to those precise embodiments, and that various other changes and modifications may be made by one skilled in the art without departing from the scope of the invention.

What is claimed is:

1. A method of forming a device having nanochannels, the method comprising:
   providing a silicon-on-insulator (SOI) wafer having a SOI layer on a buried insulator;
   forming at least one nanowire and pads in the SOI layer, wherein the nanowire is attached at opposite ends thereof to the pads, and wherein the nanowire is suspended over the buried insulator;
   forming a mask over the pads, the mask having a gap therein where the nanowire is exposed between the pads;
   forming an alternating series of metal layers and insulator layers alongside one another within the gap and surrounding the nanowire; and
   removing the nanowire to form at least one of the nanochannels in the alternating series of the metal layers and insulator layers.

2. The method of claim 1, further comprising:
   undercutting the buried insulator beneath the nanowire to suspend the nanowire over the buried insulator.

3. The method of claim 1, further comprising:
   reshaping the nanowire to give the nanowire a circular cross-sectional shape.

4. The method of claim 1, further comprising:
   thinning the nanowire.

5. The method of claim 1, wherein multiple nanowires are formed in the SOI layer, and wherein the nanowires are attached to the pads in a ladder-like configuration.

6. The method of claim 5, wherein the nanowires are spaced apart from each other horizontally by a regular distance a of from about 1 nanometer to about 5 nanometers.

7. The method of claim 1, further comprising:
   forming spacers in the gap, wherein the spacers narrow the gap;
   depositing a metal into the gap between the spacers to form a first metal layer in the series over a central portion of the nanowire; and
   removing the spacers.

8. The method of claim 7, further comprising:
   depositing an insulator on a top and sidewalls of the mask and on a top and sidewalls of the first metal layer within the gap to form at least one first insulator layer in the series.

9. The method of claim 8, further comprising:
   removing the insulator from horizontal surfaces using an anisotropic etch.

10. The method of claim 8, further comprising:
    thinning the insulator using an isotropic etch.

11. The method of claim 8, further comprising:
    depositing the metal on a top and sidewalls of the first insulator layer to form at least one second metal layer in the series.

12. The method of claim 11, further comprising:
    removing the metal from horizontal surfaces using an anisotropic etch.

13. The method of claim 11, further comprising:
    thinning the metal using an isotropic etch.

14. The method of claim 11, further comprising:
    adding at least one additional metal layer and at least one additional insulator layer to the series.

15. The method of claim 1, further comprising:
depositing a metal on a top and sidewalls of the mask within the gap to form at least one first metal layer in the series; and
depositing an insulator on a top and sidewalls of the first metal layer to form at least one first insulator layer in the series.

16. The method of claim 15, further comprising:
removing the metal and the insulator from horizontal surfaces.

17. A device comprising:
an alternating series of metal layers and insulator layers alongside one another on a buried insulator; and
a plurality of nanochannels that are horizontally aligned through the series of metal layers and insulator layers.

18. The device of claim 17, wherein the nanochannels are spaced apart from each other horizontally by a regular distance a of from about 1 nm to about 5 nm.

19. The device of claim 17, wherein the nanochannels have a circular cross-sectional shape.

20. The device of claim 17, wherein the metal is selected from the group consisting of: titanium nitride, tantalum nitride, and tungsten, and wherein the insulator is selected from the group consisting of: silicon oxide, hafnium oxide, silicon nitride, and aluminum oxide.

* * * * *